United States Patent [19]

Hellman, Jr.

[11] Patent Number: 4,802,969

[45] Date of Patent: Feb. 7, 1989

[54] GEL PLATE ASSEMBLY FOR ELECTROPHORESIS

[75] Inventor: Robert R. Hellman, Jr., Southbury, Conn.

[73] Assignee: Eastman Kodak Company, Rochester, N.Y.

[21] Appl. No.: 187,668

[22] Filed: Apr. 28, 1988

[51] Int. Cl.$^4$ .................. G01N 27/26; G01N 27/28
[52] U.S. Cl. .................. 204/299 R; 204/182.8
[58] Field of Search ............ 204/299 R, 182.8, 182.9, 204/180.1

[56] References Cited

FOREIGN PATENT DOCUMENTS 61-13044 1/1986 Japan .
61-3045 2/1986 Japan .
62-220851 9/1987 Japan .

OTHER PUBLICATIONS

Bio-Rad Price List M, 4/87.

Primary Examiner—John F. Niebling
Assistant Examiner—John S. Starsiak, Jr.
Attorney, Agent, or Firm—Dana M. Schmidt

[57] ABSTRACT

A gel plate assembly is described for use in an electrophoresis device. It comprises a glass plate having a front and rear surface, and means for confining a gel in contact with the front surface over a flow surface area. On the rear surface, there is provided in back of the flow surface area, means for evenly distributing temperature over that area, and/or mirror coating.

3 Claims, 5 Drawing Sheets

GEL PLATE ASSEMBLY FOR ELECTROPHORESIS

FIELD OF THE INVENTION

The invention concerns a gel plate assembly for use in an electrophoresis device.

BACKGROUND OF THE INVENTION

Electrophoresis is the standard technique used in nucleic acid sequencing, the technique used to plot the human genome, as reported in *Chemistry and Engineering News*, p. 22–28, dated Mar. 14, 1988. That is, DNA fragments are electrophoresed. Because of their size, this requires the use of higher power than is needed for other applications. Power usage of as much as 70 watts is common. Such power generates tremendous heat and thermal gradients in the gel plate, with the highest temperature occurring in the center lanes. Conventional vertical electrophoresis units tend to be unsatisfactory for nucleic acid sequencing, since the temperature gradients formed during the process produce artifacts that make interpretation of the results difficult, and the labeled fragments do not form uniformly straight lines. Instead, the detectable bands have the appearance of "smiles", due to the center lanes progressing faster than they should.

One problem, therefore, prior to this invention, has been to construct a sequencer that gives uniformly straight lines in the autoradiogram. This in turn requires improved temperature distribution in the gel plate.

Yet another problem with prior gel plates has been a difficulty in detecting whether or not the sample-adding pipette is in proper position within the gel plate assembly, for dispensing sample. Because of the cleanliness that is required, it has often also been difficult to ascertain whether the cavity within which the gel is to be formed, is sufficently clean.

SUMMARY OF THE INVENTION

I have designed a superior gel plate assembly which solves the aforementioned problems. This assembly features a rear plate that both provides a mirror *and* a temperature-distributing, but not dissipating, layer.

More specifically, there is provided a gel plate assembly for use in an electrophoresis device for electrophoretically separating charged compounds, such device comprising at least one support for mounting at least one such gel plate assembly. In accord with one aspect of the invention the gel plate assembly comprises a glass plate and means for confining a gel in contact with the front surface of the plate over a flow surface area, the plate having a front surface and a rear surface, the rear surface being bonded substantialy over the entire area in back of the flow surface area to means for evenly distributing temperature over the flow surface area, whereby temperature is more effectively distributed than a similar construction wherein the rear surface merely rests in contact with a temperature-distributing means.

In accord with another aspect of the invention, the gel plate assembly comprises an improved gel plate assembly comprising a glass plate and means for confining a gel in contact with the front surface of the plate over a flow surface area, the plate having a front surface and a rear surface, the rear surface being covered with a mirror coating, and means in contact with the mirror coating for providing even temperature distribution in the flow surface area of the gel plate.

Thus, it is an advantageous feature of the invention that nucleic acid sequencing reactions can be rapidly electrophoresed to produce straight dye and sample band lines, using high power generating substantial heat within the gel plate assembly.

It is a related advantageous feature of the invention that such a gel plate assembly is produced that retains the high temperature generated by high power electrophorescing of high-molecular weight fragments, and at the same time eliminates temperature-induced artifacts.

Other advantageous features will become apparent upon reference to the following description of the preferred embodiments, when read in light of the attached drawings.

DESCRIPTION OF THE PREFERRED EMBODIMENTS

The invention is described in connection with a preferred, generally vertical electrophoresis device, in which at least the bottom buffer tank is used to clamp the gel plate assembly in position. In addition, the invention is useful in other electrophoresis devices which the gel plate assembly is mounted at some angles other than the preferred angles described, and/or is clamped in place by means other than one or more buffer tanks.

Features of the electrophoresis device also described herein, other than the gel plate assembly, include subject matter that is separately claimed in the following commonly owned related applications co-filed with this application by me: "Lockable, Rotating Electrophoresis Device" bearing Ser. No. 187,117; "Improved Electrophoresis Device With Near-Vertical Gel Plates" bearing Ser. No. 187,670; and "Electrophoresis Device With Removable Buffer Tank" bearing Ser. No. 187,152.

Parts described herein as being "vertical", "horizontal", "up", "bottom" or with similar direction terms, refer to their orientation when in their normal use.

Figure 1:
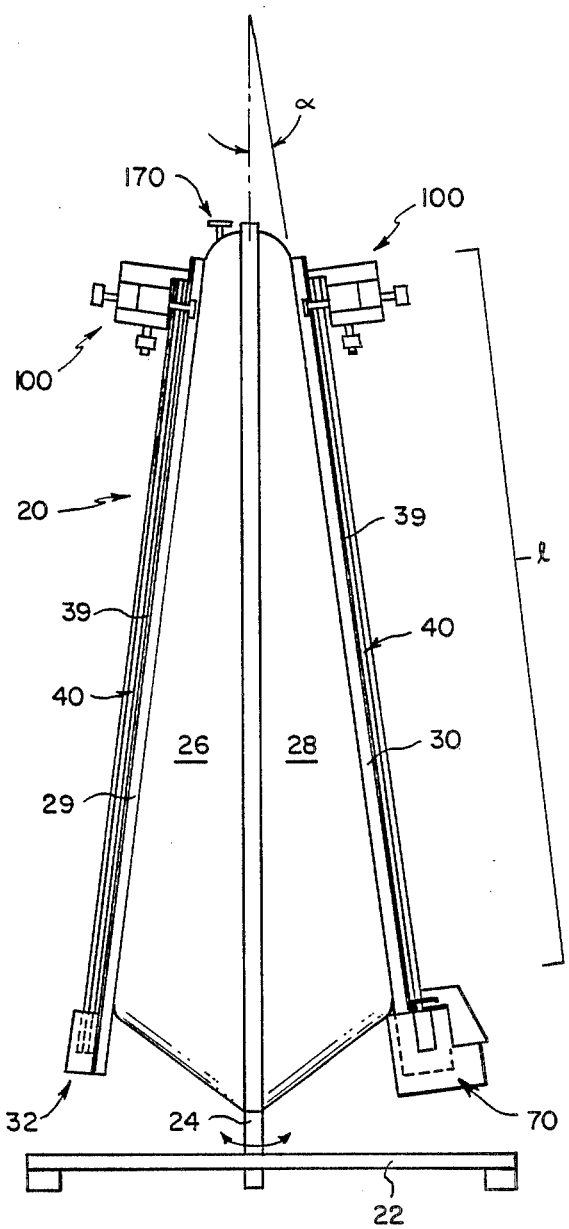
FIG. 1 is an elevational view of an electrophoresis device incorporating the features of the invention.
Figure 2:
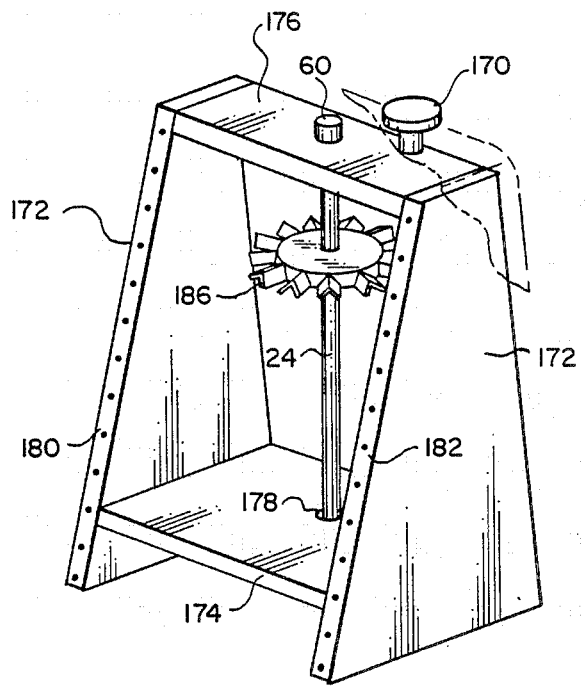
FIG. 2 is a fragmentary isometric view of the interior of the device, partly illustrating the rotatability and lockability of the device.
Figure 3:
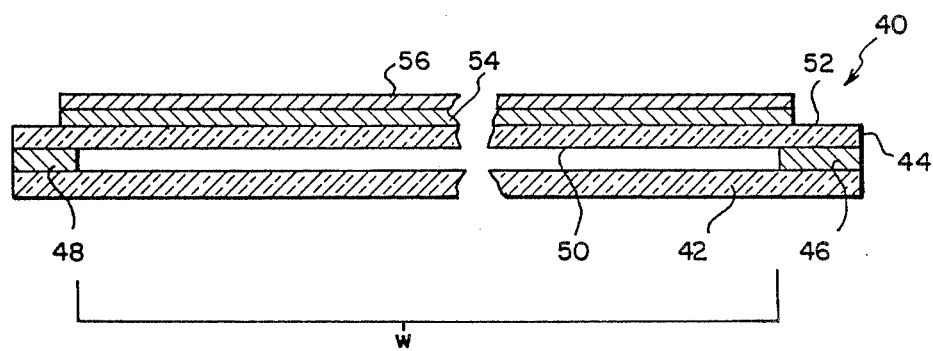
FIG. 3 is a fragmentgary sectional view of the gel plate assembly.

An electrophoresis device 20 constructed in accordance with the invention comprises, FIG. 1, a support generally comprising a base 22, a vertical post 24, two clam shell bodies 26, 28 mounted on either side of pose 24, and supporting rails 29, 30 providing a support surface for a gel plate 40 that is more completely shown in FIG. 3. Shell bodies 26 and 28 are mounted for rotation, FIG. 2, on post 24, by reason of bushing 60 that rides on the point of post 24. A locking mechanism 170 is provided, effective to releasably hold shells 26, 28 against further rotation. A pair of buffer tanks 70 and 100 are mounted at the bottom of device 20, FIG. 1, and top, respectively, as is conventional. (Only one bottom buffer tank 70 as shown in FIG. 1 for clarity, to allow illustration of trough 32.)

Figure 4:
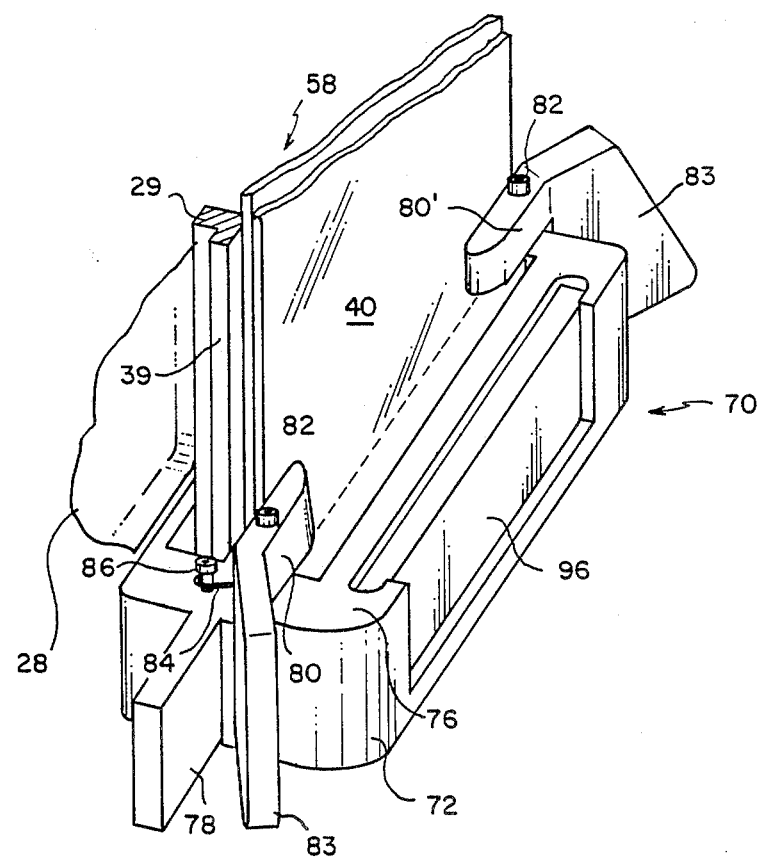
FIG. 4 is a fragmentary isometric view of the bottom buffer tank of the device.
Figure 5:
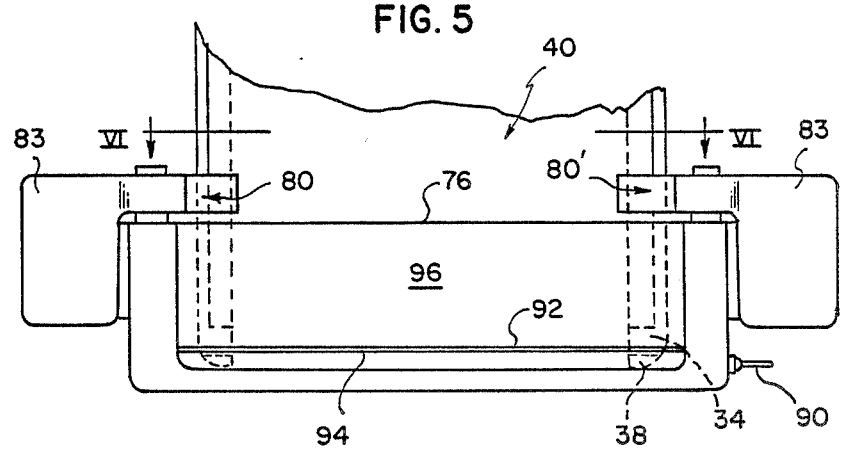
FIG. 5 is a fragmentary front elevational view of the tank of FIG. 4.
Figure 6:
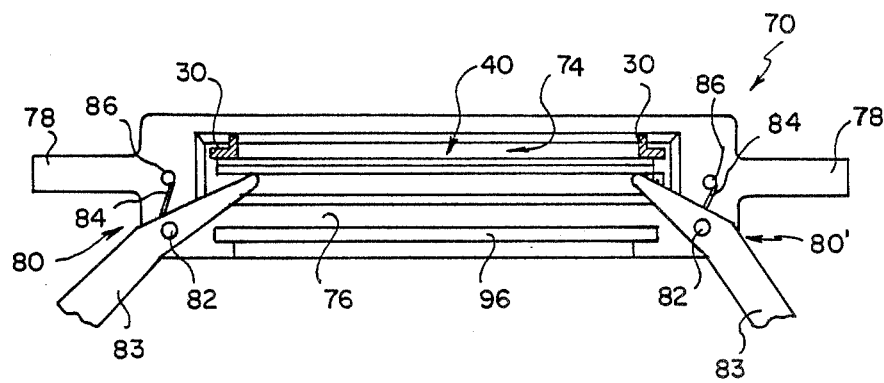
FIG. 6 is a sectional view taken along the line VI—VI of FIG. 5.

Although the supporting surface can be any suitable surface, preferably each of rails 29, 30 is a pair of rails, FIGS. 5 and 6, to provide the supporting surface for gel plate assembly 40. As is seen more clearly in FIGS. 5 and 7, the bottom of each rail features a supporting trough 32 with a front lip 34, that holds gel plate assembly 40 from falling off the rails-see also FIG. 1. Trough 32 in turn comprises a vertical shoulder 36 and a bottom ledge 38.Further, each rail 29, 30 includes a flange 39 that runs the length of the rail, FIGS. 4, 7-8, and 10, to cooperate with clamps for the buffer tanks, as described hereinafter, or with clamps for the gel plate assembly.

Each of the pairs of rails 29 or 30 is associated with its own clam shell. As such, the device permits two electrophoresis gel plate assemblies to be run simultaneously. Alternatively, additional pairs (not shown) can be mounted from the same post, the support being rotated about post 24 until the desired gel plate assembly is facing the operator.

Preferably, the gel plate supporting surfaces comprising the pair of rails is mounted to form an angle α, FIG. 1, that is inclined from the vertical by an amount between about 5° and 10°. As such, the bottom of the gel plate and buffer tank 70 are closer to the operator, when the gal plate faces the operator, than are the top of the gel plate and buffer tank 100. The advantage is that, unlike perfectly vertical plate supports of conventional devices, no care is required to hold the plate on the support while clamps are mounted in place. Instead, the plate is simply inserted into troughs 32, and leaned back against rails 29 or 30. The troughs 32 are effective in preventing the plate from dropping lower, and angle α is effective in preventing plate 40 from tipping over, until buffer tanks 70 and 100 are installed.

Angle α is preferably no less than 5°, since otherwise the angle is insufficiently different from a vertical orientation, and tipping is more likely. It is preferably no greater than 10°, since more than that tends tomake the device too bulky at the bottom.

Gel plate assembly 40, FIG. 3, is the entire assembly shown, which comprises a front plate 42, a rear plate 44, and spacers 46, 48 separating the two to allow gel (not shown) to be formed between them, as is conventional. In accord with one aspect of the invention, rear plate 44 is improved to insure superior formation and observance of dye lines in electrophoresed samples. That is, plate 44 comprises a front surface 50 and a rear surface 52. Rear surface 52 is preferably coated with a mirroring material 54, such as silver or aluminum, and a layer 56 is bonded over coating 54 substantially over the entire area in back of the flow surface area of plate assembly 40. As used herein, the bonding of layer 56 over an area "in back of the flow surface area" of the gel plate means, over an area having an extension that is coincident with, and behind, the flow surface area of the gel, wherein the electrophoresis lanes lie. This area is defined by length "1", FIG. 1, and width "w", FIG. 3. Layer 56 is selected from a material that is effective in distributing or transferring heat, for example, aluminum. This layer is tightly bonded to coating 54 over substantially all of its surface, by using any suitable means, for example an adhesive such as an acrylic adhesive. The entire laminate so formed is then preferably overcoated with a non-conductive corrosion-resistant layer for protection.

However, layer 56 is *not* used to dissipate heat from the gel plate. Rather, the supporting surfaces formed by rails 39 are deliberately held off from body 28 a distance effective to create a dead air space 58, FIGS. 4 and 8. This insulating air space insures that the heat generated by the process remains in place, thus reducing the time needed to achieve operating temperature.

Layer 56 is thus effective to transfer heat from the hotter center regions, to the peripheral regions, thereby reducing temperature gradients. As a result, dye lines form in the gel that have the desired straightness, and the results are free of thermally induced artifacts. The overall temperature, however, remains high, thus inducing the dye fronts to progress faster than is the case with water-backed units. That is, the water takes much longer to heat up to operating temperature.

The ability of the dye fronts to be processed substantially free of artifacts remains even when supplying as much as 60 watts of power to achieve temperatures as high as 70° C., when measured at the front of plate 42, producing dye front speeds as high as 0.5 cm/min.

Yet another aspect of the invention is that such a gel plate is provided with the mirrored surface 54. This surface insures that the user can more readily tell the condition of surface 50, FIG. 3. That is, the mirrored surface makes it easier to accurately introduce sample solution by pipette into the cavity between plates 42 and 44. It also helps reveal particles of dirt, if any, on surface 50 when plate 44 is being cleaned. The dye lines are also more easily detected with the mirror in place.

The gel plate assembly can be clamped onto the electrophoresis device by any clamping means, including conventional ones. Most preferably, it is mounted by clamping means that not only clamp the gel plate assembly in position, but also clamp one or both buffer tanks to the support.

Figure 7:
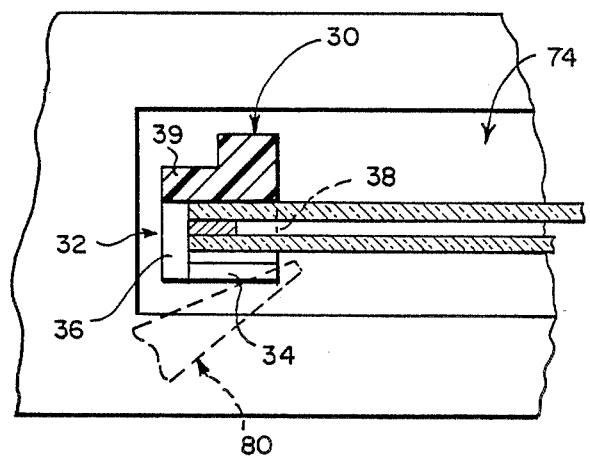
FIG. 7 is a fragmentary enlargement of the portion of FIG. 6 identified as "VII".

With respect to the bottom buffer tank 70, FIG. 4, such tank preferably comprises a cavity 74, FIGS. 6 and 7 open at top surface 76, FIG. 5. The tank has manual grasping ears 78 at either end, and two clamps 80, 80′ journalled on post 82 to top surface 76. Each clamp has a handle portion 83. A torsion spring 84 is wrapped around post 82 at one end, FIG. 6, and secured at its other end to a screw 86 attached to surface 76. As a result, clamps 80 and 80′ are biased to press inwardly-that is, clamp 80 is biased to rotate counterclockwise, FIG. 6, and 80′ to rotate clockwise.

The effect is to not only clamp tank 70 to the support at rails 29, but preferably also to clamp gel plate assembly 40 between the buffer tank and the rails 29. By this construction, it is not necessary that separate clamps or fasteners by used to hold tank 70 in place, apart from those used to clamp the gel plate in place.

Clamps 80 and 80′ work by simply grasping the clamp with the thumb and one of the ears with the fingers, and pressing against the torsion spring to release the clamp from contact with the gel plate. This in turn releases the buffer tank from engagement with rails 29 or 30, so that the buffer tank can be removed and cleaned.

As is conventional, a banana plug 90 is mounted at the side of tank 70 for connection to power wires. Inside the tank, plug 90 connects with a wire electrode 92, FIG. 5, that is supported by a rod or tube 94 that extends along the bottom of tank 70. Tube 94 and electrode 92 are preferably removable as a unit.

The front face 98 of tank 70 can be transparent, to aid in viewing the contents thereof.

Similarly, tank 100 is releasably clamped to the other end of gel plate assembly 40, FIG. 1. That is, its clamp, the details of which are not shown, preferably holds the upper end of the gel plate assembly against rails 29 and 30, by sandwiching the assembly between the rails and buffer tank 100.

The frame by which device 20 rotates comprises, FIG. 2, trapezoids 172 mounted vertically on two horizontal plates 174 and 176. Plate 174 is apertured at 178 to allow post 24 to freely extend through it. Plate 176 provides bushing 60, described hereafter. The outwardly facing edges 180, 182 of each trapezoid 172 provide the mounting support for the pairs of rails 15 mounting on the clam shell bodies, shown in phantom. Bushing 60, FIG. 11, rides on point 184 of post 24. In this fashion, the entire frame comprising plate 174, 176, bushing 60, trapezoids 172 and the attached clam shell bodies and rails, rotates on post 24.

Preferably, locking mechanism 170 temporarily prevents rotation of device 20 by the use of a two-position push latch, of a conventional construction, not shown, effective to cause a member to engage or disengage the teeth of a lock plate 186.

The invention has been described in detail with particular reference to preferred embodiments thereof, but it will be understood that variations and modifications can be effected within the spirit and scope of the invention.

What is claimed is:

1. For use in an electrophoresis device for electrophoretically separating charged compounds, the device comprising at least one support for mounting at least one gel plate assembly;

a gel plate assembly comprising a glass plate having a front surface and a rear surface, and means for confining a gel in contact with said front surface over a flow surface area, said rear surface being bonded substantially over the entire area in back of the flow surface area to means for evenly distributing temperature over said flow surface area, whereby temperature is more effectively distributed than a similar construction wherein said rear surface merely rests in contact with a temperature-distributing means, and further including a mirror coating on said rear surface, between said temperature-distributing means and said gel plate assembly.

2. A device as defined in claim 1, wherein said temperature-distributing means comprises a layer of aluminum.

3. For use in an electrophoresis device for electrophoretically separating charged comounds, the unit comprising at least one support for mounting at least one gel plate assembly, a gel plate assembly comprising a glass plate having a front surface and a rear surface, and means for confining a gel in contact with said front surface over a flow surface area, said rear surface being covered with a mirror coating, and means in contact with said mirror coating for providing even temperature distribution in the flow surface area of said gel plate assembly.

* * * * *

UNITED STATES PATENT AND TRADEMARK OFFICE
CERTIFICATE OF CORRECTION

PATENT NO. : 4,802,969
DATED : February 7, 1989
INVENTOR(S) : Hellman, Jr., Robert R.

It is certified that error appears in the above-identified patent and that said Letters Patent is hereby corrected as shown below:

Col. 2, lines 32-33 should read:
--Fig. 7 is a fragmentary enlargement of a portion of Fig. 6;--

Col. 3, lines 13-14, the sentence at those lines should read
--Further, each rail includes a flange 39 that extends the length of the rail, as shown for rail 30 in Figs. 8 & 10, to--

Col. 4, line 5, should read
--flanges 39 are deliberately held off from body 28 a distance--

Col. 4, line 55 should read
--fasteners be used to hold tank 70 in place, apart from--

Col. 5, line 1 should read
--The front face 96 of tank 70 can be transparent, to aid--

Col. 5, line 17 should read
--Bushing 60, Fig. 2, rides on a point (not shown) of post 24. In--

Signed and Sealed this

Sixteenth Day of January, 1990

Attest:

JEFFREY M. SAMUELS

*Attesting Officer*    *Acting Commissioner of Patents and Trademarks*